United States Patent [19]

Lewis et al.

[11] Patent Number: 4,973,792

[45] Date of Patent: Nov. 27, 1990

[54] CHEMICAL CONVERSION PROCESS

[75] Inventors: Jeffrey M. O. Lewis; William H. Henstock, both of Charleston, W. Va.

[73] Assignee: UOP, Des Plaines, Ill.

[21] Appl. No.: 309,927

[22] Filed: Feb. 13, 1989

Related U.S. Application Data

[63] Continuation of Ser. No. 70574, Jul. 7, 1987, abandoned.

[51] Int. Cl.$^5$ ............................ C07C 1/00; C07C 1/24
[52] U.S. Cl. ...................................... 585/638; 585/640
[58] Field of Search ..................... 208/150, 115.3, 163, 208/46, 78; 585/640, 300, 638, 639

[56] References Cited

U.S. PATENT DOCUMENTS

| | | | |
|---|---|---|---|
| 4,499,327 | 2/1985 | Kaiser | 502/60 |
| 4,513,160 | 4/1985 | Avidan et al. | 208/158 |
| 4,556,540 | 12/1985 | Benslay | 108/161 |
| 4,584,091 | 4/1986 | Farnsworth | 208/114 |
| 4,612,406 | 9/1986 | Long et al. | 585/640 |
| 4,627,911 | 12/1986 | Chen et al. | 585/640 |
| 4,666,875 | 5/1987 | Pellet et al. | 502/65 |
| 4,677,243 | 6/1987 | Kaiser | 585/639 |
| 4,814,541 | 3/1989 | Lewis | 585/733 |
| 4,861,938 | 8/1989 | Lewis et al. | 585/640 |
| 4,873,390 | 10/1989 | Lewis et al. | 585/638 |

*Primary Examiner*—Anthony McFarlane
*Attorney, Agent, or Firm*—Thomas K. McBride; John G. Tolomei; Warren K. Volles

[57] ABSTRACT

A process for catalytically converting a feedstock into a product which comprises:

(a) contacting the feedstock with a fluidized mass of solid particles comprising crystalline microporous three dimensional solid catalyst in a reaction zone at conditions effective to convert the feedstock into the product;

(b) contacting the particles in the reaction zone with a first purge medium to reduce the amount of at least one of the feedstock and the product in contact with the particles; and (c) contacting the particles in the reaction zone with regeneration medium at conditions effective to improve at least one catalytic property of the catalyst, provided that steps (a), (b) and (c) are repeated periodically.

28 Claims, No Drawings

CHEMICAL CONVERSION PROCESS

This application is a continuation of prior U.S. application Ser. No. 070,574 filed July 7, 1987, now abandoned.

FIELD OF THE INVENTION

This invention relates to a chemical conversion process employing a catalyst. More particularly, the invention relates to such a chemical conversion process employing certain defined reaction systems which provides outstanding results.

BACKGROUND OF THE INVENTION

Chemical conversions employing solid catalysts are often conducted using a fixed or fluidized bed of catalyst particles. That is, the material to be converted is contacted with a solid catalyst present in a fixed bed of particles or in a fluidized bed of particles. However, each of these two modes of operation has serious disadvantages. For example, the use of a fixed catalyst bed often results in temperature control problems which adversely affect catalyst performance. Regeneration and/or reactivation of a fixed catalyst bed can result in substantial process downtime since the chemical conversion must be stopped in order to safely treat the catalyst, e.g., while the catalyst remains in the reactor vessel. Obtaining a uniform catalyst activity distribution is also difficult with fixed catalyst beds, in particular, in situations where frequent regenerations are required.

Fluidized catalyst beds do, in general, provide better temperature control than do fixed catalyst beds. However, fluidized catalyst bed reaction systems can be much more complex than fixed catalyst bed reaction systems. For example, fluidized catalyst bed reaction systems usually involve at least two separate vessels each containing a fluidized catalyst bed, one in which to conduct the chemical conversion and one in which to regenerate the catalyst. Catalyst particles are transferred, e.g., substantially continuously transferred, between the two separate vessels. Separation devices, e.g., cyclone separators and slide valve assemblies, are often needed in both vessels to separate the catalyst particles from the feedstock/reaction product and the regeneration medium and to control the flow of catalyst between the two vessels. Such devices tend to produce increased catalyst losses through particle attrition since particle velocities within these separators are often rather high.

"Hydrocarbons from Methanol" by Clarence D. Chang, published by Marcel Dekker, Inc. N.Y. (1983) presents a survey and summary cf the technology described by its title. Chang discusses methanol to olefin conversion in the presence of molecular sieves at pages 21–26. The examples given by Chang as suitable molecular sieves for converting methanol to olefins are chabazite, erionite, and synthetic zeolite ZK-5.

Catalysts comprising one or more crystalline microporous three dimensional materials or CMSMs include naturally occuring molecular sieves and synthetic molecular sieves, together referred at as "molecular sieves," and layered clays.

Among the CMSMs that can be used to promote converting methanol to olefins are non-zeolitic molecular sieves or NZMSs, such as aluminophosphates or ALPOs, in particular silicoaluminophosphates or SAPOs disclosed in U.S. Pat. No. 4,440,871. U.S. Pat. No. 4,499,327, issued Feb. 12, 1985, discloses processes for catalytically converting methanol to light olefins using SAPOs at effective process conditions. U.S. Pat. No. 4,861,938, issued Aug. 29, 1989 discloses a process for catalytically converting a feedstock containing 1 to about 6 carbon atoms per molecule into a product wherein the catalyst is regenerated and thereafter conditioned in order to have increased effectiveness during the conversion stop. U.S. Pat. No. 4,873,390, issued Oct. 10, 1989 discloses a process for catalytically converting a feedstock into a product wherein carbonaceous material is deposited on the catalyst during the conversion and thereafter the catalyst is regenerated at conditions effective to remove only a portion of the carbonaceous material from the catalyst. U.S. Pat. No. 4,814,541, issued Mar. 21, 1989, discloses a process for catalytically converting a feedstock into product using a solid catalyst that is present in a slurry with a liquid other than the feedstock or product.

SUMMARY OF THE INVENTION

A process for catalytically converting a feedstock into a product has been discovered. In one broad aspect, the present process comprises: (a) contacting the feedstock with a fluidized mass of solid particles comprising crystalline microporous three dimensional catalyst or CMSC having the ability to promote the conversion in a reaction zone at conditions effective to convert the feedstock into the product; (b) contacting the particles in the reaction zone with a first purge medium to reduce the amount of at least one of the feedstock and product, preferably both, in contact with the particles; and (c) contacting the particles in the reaction zone with a regeneration medium at conditions effective to improve at least one catalytic property of the catalyst. Steps (a), (b) and (c) are repeated periodically, e.g., in that sequence. Preferably, the process further comprises: (d) contacting the particles in the reaction zone with a second purge medium to reduce the amount of at least one of the regeneration medium and regeneration medium product in contact with the particles and steps (a), (b), (c) and (d) are repeated periodically, e.g., in that sequence.

DISCUSSION OF THE INVENTION

The present catalytic conversion process provides substantial benefits. For example, since the particles are in fluidized motion, effective process control, in particular temperature control and catalytic activity control and/or selectivity control to the desired product, of the chemical conversion is achieved. Also, such motion may improve the effectiveness and efficiency of the purging steps, i.e., steps (b) and (d), by making the purging operation relatively less time consuming. Importantly, substantially the entire process may be conducted in the same reaction zone or vessel. Thus, the catalytic activity of the entire catalyst inventory is substantially uniform at any given point in the process. Also, the physical and mechanical wear and tear on the CMSC caused by transporting the catalyst between a separate reactor and a separate regenerator is eliminated. Because of this, the composition of the solid particles can be adjusted to improve catalytic performance without incurring substantial physical losses of catalyst. Using a single vessel, rather than a two vessel system, also reduces the amount of equipment needed to conduct the chemical conversion and to separate the various components, e.g., feedstock, product, regeneration medium, etc., from the solid particles. Chemical conversion or reaction "downtime" is reduced, particularly when, as is preferred, steps (a), (b), (c) and (d) are repeated periodically, more preferably on a substantially continuous basis.

As noted above, steps (a), (b), (c) and (d) are preferably repeated periodically, e.g., to improve the effectiveness of the catalyst in step (a). These steps are more preferably repeated in sequence, i.e., (a), (b), (c) and (d). In one embodiment, e.g., where the catalyst is susceptible to only one regeneration or reactivation before being discarded, step (a) is repeated after step (d). In this embodiment, after the catalyst is no longer acceptable for use in step (a), the catalyst may be discarded or transported for other processing, e.g., to revitalize the catalyst, before reintroducing the catalyst into the reaction zone.

The conditions at which each of steps (a), (b), (c) and (d) is conducted may be independently selected provided that each step is effective as described herein. The present system is particularly effective in situations where step (a) takes place at an average temperature within about 100° C., more preferably within about 50° C. and still more preferably within about 20° C., of the average temperature at which step (c) takes place. These preferred temperature couples allow for ease of transition between steps (a) and (c), and reduce the thermal stress on the catalyst and on the process equipment. If one of these temperature couples are employed, it is preferred that the average temperatures at which stops (b) and (d) take place be substantially within the same range. Preferably, the average temperature at which each of steps (a), (b), (c) and (d) takes place is within about 100° C., more preferably within about 50° C. and still more preferably within about 20° C., of the average temperature at which all the other such steps take place.

In one particularly useful embodiment, the conditions at which steps (a), (b) and (c), preferably steps (a), (b), (c) and (d), are conducted and the frequency of periodically repeating such steps are selected to control the temperature within the reaction zone during such steps within a predetermined range, preferably within a range defined by one of the temperature couples set forth above. Short cycles, e.g., cycles in terms of minutes, hours or days rather than months or years, are especially attractive when practicing the present invention. Such short cycles are convenient for closely controlling the reaction zone conditions during all of steps (a), (b), (c) and (d) and, in addition, allow for more effective optimization of the catalyst condition. Such short cycles also aids in maintaining a relatively constant temperature, e.g., as defined herein, in the reaction zone during all of steps (a), (b) and (c) or (a), (b), (c) and (d).

In order to operate the present process at a high degree of effectiveness, it may be desirable to at least periodically, preferably substantially continuously, withdraw a portion of the catalyst from the reaction zone for further processing to improve at least one catalytic property of the withdrawn catalyst. For example, because of the temperature constraint under which the reaction zone is operated, it may not be possible to fully regenerate (reactivate the catalyst with the regeneration medium. A portion or slip-stream of the catalyst, e.g., about 1% to about 50% of the total catalyst per reaction zone cycle, is withdrawn from the reaction zone and contacted with a medium, preferably containing oxygen, at conditions, preferably at more severe conditions, e.g., of time, temperature and/or oxygen concentration, than in step (c), effective to improve at least one catalytic property of the catalyst to produce a treated catalyst. This treated catalyst is reintroduced or returned to the reaction zone for further use in the present process.

As noted above, CMSCs are catalysts which promote chemical reactions of molecules having selected sizes, shapes or transition states. That is, CMSCs are catalysts which promote chemical reactions of feedstock molecules which conform to a given molecular size, molecular shape or transition stage constraint. Different CMSCs have different size/shape/transition stage constraints depending on the physical structure and chemical composition, for example, the effective diameter of the pores, of the catalyst. Thus, the particular CMSC chosen for use depends on the particular feedstock employed, and the particular chemical (reaction) and product desired. Preferably, the CMSC has a substantially uniform pore structure, e.g., substantially uniformly sized and shaped pores. CMSCs include, for example, layered clays; zeolitic molecular sieves and non-zeolitic molecular sieves or NZMSs.

The presently useful NZMSs include molecular sieves embraced by an empirical chemical composition, on an anhydrous basis, expressed by the formula:

where "Q" represents at least one element present as a framework oxide unit "$QO_2{}^n$" with charge "n" where "n" may be $-3, -2, -1, 0$ or $+1$; "R" represents at least one organic templating agent present on the intracrystalline pore system; "m" represents the molar amount of "R" present per mole of $(Q_wAl_xP_ySi_z)O_2$ and has a value from zero to about 0.3; and "w", "x", "y" and "z" represent the mole fractions of $QO_2{}^n$, $AlO_2{}^-$, $PO_2{}^+$, $SiO_2$, respectively, present as framework oxide units. "Q" is characterized as an element having a mean "T—O" distance in tetrahedral oxide structures between about 1.51 Å and about 2.06 Å. "Q" has a cation electronegativity between about 125 kcal/g-atom to about 310 kcal/gm-atom and "Q" is capable of forming stable Q—O—P, Q—O—Al or Q—O—Q bonds in crystalline three dimensional oxide structures having a "Q—O" bond dissociation energy greater than about 59 kcal/g-atom at 298° K.[1]; and "w", "x", "y" and "z" represent the mole fractions of "Q", aluminum, phosphorus and silicon, respectively, present as framework oxides said mole fractions being within the limiting compositional values or points as follows:

w is equal to 0 to 99 mole percent;
y is equal to 1 to 99 mole percent;
x is equal to 1 to 99 mole percent; and
z is equal to 0 to 99 mole percent.

[1] See the discussion at pages 8a, 8b and 8c of EPC Publication 0 159 624, published Oct. 30, 1985, about the characterization of "EL" and "M". Such are equivalent to Q as used herein.

The "Q" of the "SAPSO" molecular sieves of formula (I) may be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. Combinations of the elements are contemplated as representing Q, and to the extent such combinations are present in the structure of a QAPSO they may be present in molar fractions of the Q component in the range of 1 to 99 percent thereof. It should be noted that formula (I) contemplates the non-existence of Q and Si. In such case, the operative structure is that of aluminophosphate or AlPO₄. Where z has a positive value, then the operative structure is that of silicoaluminophosphate or SAPO. Thus, the term QAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as herein discussed. However, in the contemplation that molecular sieves of the QAPSO variety will be invented in which Q will be another element or elements, then it is the intention to embrace the same as a suitable molecular sieve for the practice of this invention.

Illustrations of QAPSO compositions and structures are the various compositions and structures described in the patents and patent applications set forth in Table A, which follows, and by Flanigen et al., in the paper entitled, "Aluminophosphate Molecular Sieves and the Periodic Table," published in the "New Developments and Zeolite Science Technology" Proceedings of the 7th International Zeolite Conference, edited by Y. Murakami, A. Sijima and J. W. Ward, pages 103–112 (1986):

TABLE A

Patent or Pat. Applic. No. U.S. Pat. No. 4,567,029

Subject Matter of Patent or Patent Application.

MAPO's are crystalline metal aluminophosphates having a three-dimensional microporous framework structure of $MO_2^{-2}$, $AlO_2^-$ and $PO_2^+$ tetrahedral units and having an empirical chemical composition on an anhydrous basis expressed by the formula $mR:(M_xAl_yP_z)O_2$; where R represents at least one organic templating agent present in the intracrystalline pore system; m has a typical value of from 0 to 0.3 and the moles of R present per mole of $(M_xAL_yP)O_2$; M represents magnesium, manganese, zinc or cobalt, x, y and z represent the mole fractions of M, aluminum and phosphorus, respectively, present as tetrahedral oxides. The fractions are such that they are within a tetragonal compositional area defined by points ABC and D of FIG. 1 of the drawings of the patent.

This patent, at column 6, describes the use of aluminophosphates as a source of phosphorus (lines 26–28) and as a source of aluminum (lines 38–40), and the use of seed crystals to aid in the crystallization of the desired molecular sieve (lines 59–63). Example 85 depicts the use of MAPO-36 as a seed for making MnAPO-36. The chemical composition of the MnAPO-36 fails to reveal the presence of any magnesium.

U.S. Pat. No. 4,440,871

SAPO molecular sieves are a general class of microporous crystalilne silicoaluminophosphates. The pores have a nominal diameter of greater than about 3 Å. The "essentially empirical composition" is $mR:(Si_xAl_yP_z)O_2$, where R represents at least one organic templating agent present in the intracrystalline pore system; m has a typical value of from 0 to 0.3 and represents the moles of R present per mole of $(Si_xAl_yP_z)O_2$; x, y and z represent the mole fractions of silicon, aluminum and phosphorus, respectively, present as tetrahedral oxides. The fractions are such that they are within a pentagonal compositional area defined by points A, B, C, D and E of the ternary diagram of FIG. 1 and preferably within the pentagonal compositional area defined by points a, b, c, d and e of FIG. 2, of the drawings of the patent. The SAPO molecular sieves have a characteristic x-ray powder diffraction pattern which contains at least the d-spacings set forth in any one of Tables I, III, V, VII, IX, XI, XIII, XV, XVII, XIX, XXI, XXIII or XXV of the patent. Further, the as-synthesized crystalline silicoaluminophosphates of the patent may be calcined at a temperature sufficiently high to remove at least some of any organic templating agent present in the intracrystalline pore system as a result of such synthesis. The silicoaluminophosphates are generally referred to therein as "SAPO", as a class, or as "SAPO-n" wherein "n" is an integer denoting a particular SAPO as its preparation is reported in the patent.

The U.S. patent speaks at column 8, lines 12–16 of employing seed crystals to generate SAPO species. That technique is described in examples 22, 51 and 53.

U.S. Ser. No. 600,312 filed Apr. 13, 1984, commonly assigned, EPC Public. 0 159 624, published Oct. 30, 1985

ELAPSO molecular sieves have the units $ELO_2^n$, $AlO_2^-$, $PO_2^+$, $SiO_2$ in the framework structure and have an empirical chemical composition on an anhydrous basis expressed by the formula:

$$mR:(EL_wAl_xP_ySi_z)O_2$$

where "EL" represents at least one element present as a framework oxide unit "$ELO_2^n$" with charge "n" where "n" may be −3, −2, −1, 0 or +1; "R" represents at least one organic templating agent present on the intracrystalline pore system; "m" represents the molar amount of "R" present per mole of $(EL_wAl_xP_ySi_z)O_2$ and has a value from zero to about 0.3; and "w", "x", "y" and "z" repesent the mole fractions of $ELO_2^n$, $ALO_2$-, $PO_2$t, $SiO_2$, respectively, present as framework oxide units. "EL" is characterized as an element having (a) a mean "T—O" distance in tetrahedral oxide structures between about 1.51 Å and about 2.06 Å, (b) a cation electronegativity between about 125 kcal/g-atom to about 310 kcal/gm-atom and (c) a capability of forming stable M—O—P, M—O—Al or M—O—M bonds in crystalline three dimensional oxide structures having a "m—O" bond dissociation energy greater than about 59 kcal/g-atom at 298° K. "w", "x", "Y" and "z" represent the mole fractions of "EL", aluminum, phosphorus and silicon, respectively, present as framework oxides. The mole fractions are within the limiting compositional values or points as follows:

| Point | Mole Fraction | | |
| --- | --- | --- | --- |
| | x | y | (z + w) |
| A | 0.60 | 0.39−(0.01 p) | 0.01(p + 1) |
| B | 0.39−(0.01p) | 0.60 | 0.01(P + 1) |
| C | 0.01 | 0.60 | 0.39 |
| D | 0.01 | 0.01 | 0.98 |
| E | 0.60 | 0.01 | 0.39 | where "p" is an integer corresponding to the number of elements which "EL" represents in the $(EL_wAl_xP_ySi_z)O_2$ composition.

The "EL" of the "ELAPSO" molecular sieves may be defined as representing at least one element capable of forming a framework tetrahedral oxide and is preferably selected from the group consisting of arsenic, beryllium, boron, chromium, cobalt, gallium, germanium, iron, lithium, magnesium, manganese, titanium and zinc and "w", "x", "y" and "z" represent the mole fractions of "EL", aluminum, phosphorus and silicon, respectively, present at tetrahedral oxides in which the mole fractions are within the limiting compositional values or points as follows:

| Point | Mole Fraction | | |
|---|---|---|---|
| | x | y | (z + w) |
| a | 0.60 | 0.39−(0.01 p) | 0.01(p + 1) |
| b | 0.39−(0.01 p) | 0.60 | 0.01(p + 1) |
| c | 0.10 | 0.55 | 0.35 |
| d | 0.55 | 0.10 | 0.35 | where "p" is as above defined.

The EP publication at page 16 discloses the use of crystalline and amorphous aluminophosphate as a source of phosphorus and aluminum and at page 17 describes seeding the reaction mixture. Examples 11A, 12A, 93A–103A, 5B, 6B, 55B, 58B, 59B, 50D–56D, 59D–62D and 12F–15F depict the use of seed crystals.

U.S. Pat. No. 4,500,651, patented Feb. 19, 1985

TAPO molecular sieves comprise three-dimensional microporous crystalline framework structures of [TiO$_2$], [AlO$_2$] and [PO$_2$] tetrahedral units which have a unit empirical formula on an anhydrous basis of:

$$mR:(Ti_xAl_yP_z)O_2 \qquad (1)$$

wherein "R" represents at least one organic templating agent present in the intracrystalline pore system; "m" represents the moles of "R" present per mole of (Ti$_x$Al$_y$P$_z$)O$_2$ and has a value of from zero to 5.0, the maximum value in each case depending upon the molecular dimensions of the templating agent and the available void volume of the pore system of the particular titanium molecular sieve; "x", "y" and "z" represent the mole fractions of titanium, aluminum and phosphorus, respectively, present as tetrahedral oxides, representing the following values for "x", "y" and "z":

| Point | Mole Fraction | | |
|---|---|---|---|
| | x | y | (z + w) |
| A | 0.001 | 0.45 | 0.549 |
| B | 0.88 | 0.01 | 0.11 |
| C | 0.98 | 0.01 | 0.01 |
| D | 0.29 | 0.70 | 0.01 |
| E | 0.0001 | 0.70 | 0.299 |

The parameters "x", "y" and "z" are preferably within the following values for "x", "y" and "z":

| Point | Mole Fraction | | |
|---|---|---|---|
| | x | y | (z + w) |
| a | 0.002 | 0.499 | 0.499 |
| b | 0.20 | 0.40 | 0.40 |
| c | 0.20 | 0.50 | 0.30 |
| d | 0.10 | 0.60 | 0.30 |
| e | 0.002 | 0.60 | 0.398 |

The TAPO molecular sieves are generally further characterized by an intracrystalline adsorption capacity for water at 4.6 torr and about 24° C., of about 3.0 weight percent. The adsorption of water has been observed to be completely reversible while retaining the same essential framework topology in both the hydrated and dehydrated state.

The U.S. patent at column 8, lines 65–68, and column 9, lines 15–18, discusses the use of crystalline amorphous aluminophosphate as a source of phosphorus and aluminum. At column 6, lines 1–5, seeding is described as facilitating the crystallization procedure. Comparative example 44 describes a composition of amorphous TiO$_2$ and 95 wt. % AlPO$_4$18 without an indication of how the composition was prepared.

U.S. Pat. No. 4,684,617, EPC Publication No. 0 161 488, published Nov. 21, 1985

The TiAPSO molecular sieves have three-dimensional microporous framework structures of TiO$_2$, AlO$_2^-$, PO$_2^{-2}$ and SiO$_2$ tetrahedral oxide units having an empirical chemical composition on an anhydrous basis expressed by the formula:

$$mR:(Ti_wAl_xP_ySi_z)O_2$$

wherein "R" represents at least one organic templating agent present in the intracrystalline pore system; "m" represents the molar amount of "R" present per mole of (Ti$_w$Al$_x$P$_y$Si$_z$)O$_2$ and has a value of from zero to about 0.3; and "w", "x", "y" and "z" represent the mole fractions of titanium, aluminum, phosphorus and silicon, respectively, present as tetrahedral oxides and each has a value of at least 0.01. The mole fractions "w", "x", "y" and "z" are generally defined in respect to the ternary diagram of FIG. 1 of the applications as being within the following limiting compositional values or points:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a subclass of TiAPSO molecular sieves the values "w", "x", "y" and "z" in the above formula are within the tetragonal compositional area defined by points a, b, c and d of the ternary diagram of FIG. 2 of the aplications, said points a, b, c and d representing the following values for "w", "x", "y" and "z":

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication, at page 13, describes the use of crystalline or amorphous aluminophosphate as a source of phosphorus and aluminum and, at page 14, points out that seeding the reaction mixture facilitates the crystallization procedure.

U.S. Pat. No. 4,554,143, patented Nov. 19, 1985

Ferroaluminophosphates (FAPO's) are disclosed in U.S. Pat. No. 4,554,143, incorporated herein by reference, and have a three-dimensional microporous crystal framework structure of AlO₂, FeO₂ and PO₂ tetrahedral units and have an essential empirical chemical composition, on an anhydrous basis, of:

mR:(Fe$_x$Al$_y$P$_z$)O$_2$ wherein "R" represents at least one organic templating agent present in the intracrystalline pore system; "m" represents the moles of "R" present per mole of (Fe$_x$Al$_y$P$_z$)O$_2$ and has a value of from zero to 0.3, the maximum value in each case depending upon the molecular dimensions of the templating agent and the available void volume of the pore system of the particular ferroaluminophosphate involved; "x", "y" and "z" represent the mole fractions of iron, aluminum and phosphorus, respectively, present as tetrahedral oxides, representing the following values for "x", "y" and "z":

| Point | Mole Fraction | | |
|---|---|---|---|
| | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the ferroaluminophosphates the values of "x", "y" and "z" in the formula above are representing the following values of "x", "y" and "z":

| Point | Mole Fraction | | |
|---|---|---|---|
| | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The iron of the FeO₂ structural units can be in either the ferric or ferrous valence state, depending largely upon the source of the iron in the synthesis gel. Thus, a FeO₂ tetrahedron in the structure can have a net charge of either −1 or −2.

The patent indicates at column 5, lines 43–45 and 54–56, that crystalline amorphous aluminophosphate may be used as a source of phosphorus and aluminum and at column 6, lines 1–5, describes seeding of the reaction mixture as facilitating the crystallization procedure.

U.S. Pat. No. 4,683,217 EPC Publication No. 0 161 491, published Nov. 21, 1985

The FeAPSO molecular sieves have a three-dimensional microporous crystal framework structures of FeO₂⁻² (and/or FeO₂), AlO₂, PO₂ and SiO₂ tetrahedral oxide units and having a unit empirical formula, on an anhydrous basis, of:

mR:(Fe$_w$Al$_x$P$_y$Si$_z$)O$_2$     (1)

wherein "R" represents at least one organic templating agent present in the intracrystalline pore system; "m" represents the moles of "R" present per mole of (Fe$_w$Al$_x$P$_y$Si$_z$)O$_2$ and has a value of from zero to about 0.3; the maximum value of "m" in each case depends upon the molecular dimensions of the templating agent and the available void volume of the pore system of the particular molecular sieve involved; and "w", "x", "y" and "z" represent the mole fractions of iron, aluminum, phosphorus and silicon, respectively, present as tetrahedral oxides, said mole fractions being such that they are within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| Point | Mole Fraction | | |
|---|---|---|---|
| | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication, at page 12, describes the use of seeding the reaction mixture to facilitate the crystallization procedure. At page 18, the publication describes the use of crystalline amorphous aluminophosphates as a source of phosphorus and aluminum in making the molecular sieve.

U.S. Ser. No. 600,170, EPC Publication No. 0 158 975, published Oct. 23, 1985

The ZnAPSO molecular sieves of U.S. Ser. No. 600,170, filed Apr. 13, 1984 comprise framework structures of ZnO₂⁻², AlO₂⁻, PO₂⁺ and SiO₂ tetrahedral units havings an empirical chemical composition on an anhydrous Oct. basis expressed by the formula:

mR:(Zn$_w$Al$_x$P$_y$Si$_z$)O$_2$ wherein "R" represents at least one organic templating agent present in the intracrystalline pore system; "m" represents the molar amount of "R" present per mole of (Zn$_w$Al$_x$P$_y$Si$_z$)O$_2$ and has a value of zero to about 0.3; and "w", "x", "y" and "z" represent the mole fractions of zinc, aluminum, phosphorus and silicon, respectively, present as tetrahedral oxides and each has a value of at least 0.01. The mole fractions "w", "x", "y" and "z" are generally defined being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

In a preferred subclass of ZnAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication at page 13 discloses that crystalline or amorphous aluminophosphate may be used as a source of phosphorus or aluminum and at page 14 indicates that seeding of the reaction mixture with said crystals facilitates the crystallization procedure. Examples 12-15 are stated to employ the seeding procedure.

U.S. Pat. No. 4,758,419 EPC Publication 0 158 348, published Oct. 16, 1985

The MgAPSO molecular sieves have three-dimensional microporous framework structures of $MgO_2^{-2}$, $AlO_2^-$, $PO_2^+$ and $SiO_2$ tetrahedral oxide units and have an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value from zero to about 0.3; and "w", "x", "y" and "z" represent the mole fractions of magnesium, aluminum, phosphorus and silicon, respectively, present as tetrahedral oxides and each preferably has a value of at least 0.01. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

In a preferred subclass of the MgAPSO molecular sieves the values "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

This publication depicts seeding to generate product at page 14 and in examples 5, 6, 55, 58 and 59.

U.S. Pat. No. 4,686,092 EPC Publication 0 161 490, published Nov. 11, 1985

The MnAPSO molecular sieves of U.S. Ser. No. 600,175, filed Apr. 13, 1984 have a framework structure of $MnO_2^2$, $AlO_2$, $PO_2$, and $SiO_2$ tetrahedral units having an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w" "x" "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The values of w, x, y and z may be as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The publication at page 13 describes the use of crystal or amorphous aluminophosphate as a source of phosphorus or aluminum, and at page 14 characterizes the use of said crystals to facilitate the crystallization procedure. Examples 54-56 and 59-62 state said crystals were used in the manufacture of the MnAPSO products.

U.S. Pat. No. 4,744,970 EPC Publication 0 161 489, published Nov. 21, 1985

The CoAPSO molecular sieves of U.S. Ser. No. 600,174, filed Apr. 13, 1984 have three-dimensional microporous framework structures of $CoO_2^2$, $AlO_2$, $PO_2$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represents the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| | Mole Fraction | | |
|---|---|---|---|
| Point | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |

| | Mole Fraction | | |
|---|---|---|---|
| Point | x | y | (z + w) |
| E | 0.60 | 0.01 | 0.39 |

In a preferred subclass of the CoAPSO molecular sieves the values of "w", "x", "y" and "z" in the above formula are within the limiting compositional values or points as follows:

| | Mole Fraction | | |
|---|---|---|---|
| Point | x | y | (z + w) |
| a | 0.55 | 0.43 | 0.02 |
| b | 0.43 | 0.55 | 0.02 |
| c | 0.10 | 0.55 | 0.35 |
| d | 0.55 | 0.10 | 0.35 |

The EP publication at page 13 depicts the use of crystalline amorphous aluminophosphate as a source of phosphorus and aluminum and at page 14 states that seeding the reaction mixture facilitates the crystallization procedure. Examples 11, 12, 13, 93 and 97–103 depict the use of seed crystals. U.S. Pat. Nos. 599,771; 588,776; 599,807; 599,809; 599,811; 59,812; 599,813; 600,166; each filed Apr. 13, 1984, all now abandoned U.S. Pat. No. 4,686,093; EPC Publication 0,158,976, published Oct. 21, 1985.

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,028. Members of this novel class of compositions have a three-dimensional microporous crystal framework structure of $MO_2$, $AlO_2$ and $PO_2$ tetrahedral units and have the essentially empirical chemical composition, on an anhydrous basis, of:

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y" and "z" represent the mole fractions of the metal "M", (i.e., magnesium, manganese, zinc and cobalt), aluminum and phosphorus, respectively, present as tetrahedral oxides, said mole fractions being such that they are representing the following values for "x", "y" and "z":

| | Mole Fraction | | |
|---|---|---|---|
| Point | x | y | (z + w) |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. In a preferred subclass of the metal aluminophosphates of this invention, the values of "x", "y" and "z" in the formula above are representing the following values for "x", "y" and "z":

| | Mole Fraction | | |
|---|---|---|---|
| Point | x | y | (z + w) |
| a | 0.01 | 0.52 | 0.47 |
| b | 0.01 | 0.39 | 0.60 |
| c | 0.25 | 0.15 | 0.60 |
| d | 0.25 | 0.40 | 0.35 |

The as-synthesized compositions are capable of withstanding 350° C. calcination in air for extended periods, i.e., at least 2 hours, without becoming amorphous.

The EP publication at pages 14 and 15 depicts the use of crystalline and amorphous aluminophosphate as a source of, phosphorus and aluminum and at page 15 states that seeding the reaction mixture facilitates the crystallization procedure. Example 8 discloses seeding of crystals.

EPC Applic. 85104386.9, filed Apr. 11, 1985 (EPC Publication No. 0158976, published Oct. 13, 1985) and EPC Applic. 85104388.5, filed Apr. 11, 1985 (EPC Publication No. 158348, published Oct. 16, 1985)

"ELAPO" molecular sieves are a class of crystalline molecular sieves in which at least one element capable of forming a three-dimensional microporous framework form crystal framework structures of $AlO_2$, $PO_2$ and $MO_2$ tetrahedral oxide units wherein "$MO_2$" represents at least one different element (other than Al or P) present as tetrahedral oxide units "$MO_2$" with charge "n" where "n" may be $-3$, $-2$, $-1$, 0 or $+1$. The members of this novel class of molecular sieve compositions have crystal framework structures of $AlO_2$, $PO_2$ and $MO_2$ tetrahedral units and have an empirical chemical composition on an anhydrous basis expressed by the formula:

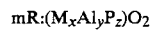

wherein "R" represents at least one organic templating agent present in the intracrystalline pore system; "m" represents the molar amount of "R" present per mole of $(M_xAl_yP_z)O_2$; "M" represents at least one element capable of forming framework tetrahedral oxides; and "x", "y" and "z" represent the mole fractions of "M", aluminum and phosphorus, respectively, present as tetrahedral oxides. "M" is at least one different elements ($M_1$) such that the molecular sieves contain at least one framework tetrahedral units in addition to $AlO_2$ and $PO_2$. "M" is at least one element selected from the group consisting of arsenic, beryllium, boron, chromium, gallium, germanium and lithium, and when "M" denotes two elements the second element may be one of the aforementioned and/or is at least one element selected from the group consisting of cobalt, iron, magnesium, manganese, titanium and zinc.

The ELAPO molecular sieves are generally referred to herein by the acronym or "ELAPO" to designate element(s) "M" in a framework of $AlO_2$, $PO_2$ and $MO_2$ tetrahedral oxide units. Actual class members will be identified by replacing the "EL" of the acronym with the elements present as $MO_2$ tetrahedral units.

When "M" denotes two elements "M" may also be at least one element selected from the group consisting of cobalt, iron, magnesium, manganese, titanium and zinc. For example, in each instance "M" includes at least one of the first group of elements, e.g., As, Be, etc., and when two or more elements are present, the second and further elements may be selected from the first group of elements and/or the second group of elements, as above discussed.

The ELAPO molecular sieves have crystalline three-dimensional microporous framework structures of $AlO_2$, $PO_2$ and $MO_2$ tetrahedral units and have an empirical chemical composition on an anhydrous basis expressed by the formula:

$$mR:(M_xAl_yP_z)O_2;$$

wherein "R" represents at least one organic templating agent present in the intracrystalline pore system; "m" represents the molar amount of "R" present per mole of $(M_xAl_yP_z)O_2$ and has a value of zero to about 0.3; "M" represents at least one element capable of forming framework tetrahedral oxides where "M" is at least one element selected from the group consisting of arsenic, beryllium, boron, chromium, gallium, germanium and lithium. When "M" includes an additional element such additional elements "M" may be at least one element selected from the group consisting of cobalt, iron, magnesium, manganese, titanium, and zinc.

The relative amounts of element(s) "M", aluminum and phosphorus are expressed by the empirical chemical formula (anhydrous):

$$mR:(M_xAl_yP_z)O_2$$

where "x", "y" and "z" reprresent the mole fractions of said "M", aluminum and phosphorus. The individual mole fractions of each "M" (of when M denotes two or more elements, $M_1$, $M_2$, $M_3$, etc.) may be represented by "$x_1$", "$x_2$", "$x_3$", etc. wherein "$x_1$", "$x_2$", and "$x_3$", and etc. represent the individual mole fractions of elements $M_1$, $M_2$, $M_3$, and etc. for "M" as above defined. The values of "$x_1$", "$x_2$", "$x_3$", etc. are as defined for "x" hereinafter, where "$x_1$"+"$x_2$"+"$x_3$"... = "x" and where $x_1$, $x_2$, $x_3$, etc. are each at least 0.01.

The ELAPO molecular sieves have crystalline three-dimensional microporous framework structures of $MO_2$, $AlO_2$ and $PO_2$ tetrahedral units having an empirical chemical composition on an anhydrous basis expressed by the formula:

$$mR:(M_xAl_yP_z)O_2$$

wherein "R" represents at least one organic templating agent present in the intracrystalline pore system; "m" represents a molar amount of "R" present per mole of $(M_xAl_yP_z)O_2$ and has a value of zero to about 0.3; "M" represents at least one different element (other than Al or P) capable of forming framework tetrahedral oxides, as hereinbefore defined, and "x", "y" and "z" represent the mole fractions of "M", aluminum and phosphorus, respectively, present as tetrahedral oxides; said mole fractions "x", "y" and "z" being generally defined as within the following values for "x", "y", and "z":

| Point | Mole Fraction | | |
|-------|------|------|---------|
|       | x    | y    | (z + w) |
| A | 0.02 | 0.60 | 0.38 |
| B | 0.02 | 0.38 | 0.60 |
| C | 0.39 | 0.01 | 0.60 |
| D | 0.98 | 0.01 | 0.01 |

| Point | Mole Fraction | | |
|-------|------|------|---------|
|       | x    | y    | (z + w) |
| E | 0.39 | 0.60 | 0.01 |

In a preferred sub-class of the ELAPOs of this invention, the values of "x", "y" and "z" in the formula above are within the following values for "x", "y" and "z":

| Point | Mole Fraction | | |
|-------|------|------|---------|
|       | x    | y    | (z + w) |
| a | 0.02 | 0.60 | 0.39 |
| b | 0.02 | 0.38 | 0.60 |
| c | 0.39 | 0.01 | 0.60 |
| d | 0.60 | 0.01 | 0.39 |
| e | 0.60 | 0.39 | 0.01 |
| f | 0.39 | 0.60 | 0.01 |

U.S. Pat. No. 4,310,440

ALPO's are the basic and simplest of the crystalline aluminophosphates. They each having a framework structure whose chemical composition expressed in terms of mole ratios of oxides is:

$$Al_2O_3:1.0\pm 0.2P_2O_5:$$

each of said framework structures being microporous in which the pores are uniform and have nominal diameters within the range of about 3 to about 10 Å, an intracrystalline adsorption capacity for water at 4.6 torr and 24° C. of at least 3.5 weight percent, the adsorption and desorption of water being completely reversible while retaining the same essential framework topology in both the hydrated and dehydrated state.

U.S. paten application Ser. Nos. 600,168, (abandoned) 600,182, (abandoned) 600,183; U.S. Pat. No. 4,741,892; European Patent Publ. No. 0 158 350, publ. Oct. 16, 1985.

SENAPSO are quinary and senary molecular sieves that have framework structures of at least two elements having tetrahedral oxide units "$MO_2{}^n$" and having $AlO_2{}^-$, $PO_2{}^+$ $SiO_2$ tetrahedral oxide units, where "n" is $-3$, $-2$, $-1$, 0 or $+1$, and have an empirical chemical composition on an anhydrous basis expressed by the formula:

$$mR:(M_wAl_xP_ySi_z)O_2$$

wherein "R" represents at least one organic templating agent present in the intracrystalline pore system; "m" represents the molar amount of "R" present per mole of $(M_wAl_xP_ySi_z)O_2$ and has a value of from 0 to about 0.3; "M" represents at least two elements selected from the group consisting of arsenic, beryllium, boron, chromium, cobalt, gallium, germanium, iron, lithium, magnesium, manganese, titanium, vanadium, and zinc; "n" is as above defined; and "w", "x", "y" and "z" represent the mole fractions of elements "M", aluminium, phosphorus and silicon, respectively, present as tetrahedral oxides, each having a value of at least 0,01.

The publication, at pages 14–15, generally describes seeding reaction mixtures to form the desired product.

Zeolitic molecular sieves may be represented by the general formula:

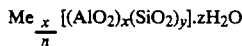

where Me is a metal cation, x/n is the number of exchangeable metal cations of valence n, x is also the number of aluminum ions combined in the form of aluminate, y is the number of silicon atoms and z is the number of water molecules, removal of which produces the characteristic pore or channel system. The ratio z/x is a number from 1 to 5, usually from 1 to 2.

Typical of the zeolitic molecular sieves are chabazite, faujasite levynite, Linde Type A, gismondine, erionite, sodalite, Linde Type X and Y, analcime, gmelinite, harmotome, levynite, mordenite, epistilbite, heulandite, stilbite, edingtonite, mesolite, natrolite, scolecite, thomsonite, brewsterite, laumontite, phillipsite, the ZSM's (e.g., ZSM-5[2], ZSM-20[3], ZSM-12[4], ZSM-34[5], etc.) and Beta[6] and the like.

[2]See U.S. Pat. No. 3,702,886. [3]See U.S. Pat. No. 3,972,983. [4]See U.S. Pat. No. 3,832,449. [5]See U.S. Pat. No. 4,079,095. [6]See U.S. Pat. No. 3,308,069 and U.S. Reissue Pat. No. 28,341.

Typical of suitable zeolitic molecular sieves employable in the practice of this invention are the following:

Zeolites- A, AgX, AgY, AlHY, alkylammonium X and Y, BaX, BaY, BeY, Ca-A, Ca-near faujasite, Ca-HX, Ca-X, Ca-Y, CdX, CdY, CeY, CoA, CoX, CoY, CrY, CsL, CsX, CsY, Cu-X, Cu-Y, Cu-diethylammonium Y, Cu-ethylammonium Y, Fe-X, Fe-Y, group IAX, group IAY, group IIAY, HY, KL, KX, KY, L, La-X, La-Y, LiA, LiX, LiY, LZ-10, LZ-210, MgHY, MgNa, MgNH$_4$Y, MgX, MgY, MnX, MnY, Na-A, Na-near faujasite, Na-L, Na-X, Na-Y, NH$_4$L, NH$_4$X, NH$_4$Y, Ni-A, Ni-X, Ni-Y, omega, PdY, phosphate, Pt, ultra-stable Y, tetramethylammonium Y, TlX, triethylammonium Y, X, Y, Y-82, ZK-5, Zn-mordenite, Zn-X, An-Y, the ZSM's, supra, and the like.

Other zeolitic CMSCs useful in the present invention include boron-treated aluminosilicates, such as described in U.S. Pat. NO. 4,613,720. Other NZMSs include the silica molecular sieves, such as silicalite as depicted in U.S. Pat. No. 4,061,724.

The average diameter of the pores of the presently useful CMSCs is preferably in the range of about 3 angstroms to about 15 angstroms as determined by measurements described in "Zeolite Molecular Sieves" by Donald W. Breck, published by John Wiley & Sons, New York, 1974. This average diameter is referred to as the average effective diameter. When the feedstock and desired product or products are relatively small, e.g., organic components containing 1 to about 10 and preferably 1 to about 4 carbon atoms per molecule, the CMSC preferably has pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the CMSC and adsorption of the adsorbate is over three percent by weight of the adsorbate based on the weight of the CMSC. Certain of the CMSCs useful in the present invention have pores with an average effective diameter in the range of about 3 angstroms to about 5 angstroms.

The presently useful catalysts ar incorporated into solid particles in which the catalyst is present in an amount effective to promote the desired chemical conversion. In one embodiment, the solid particles comprise a catalytically effective amount of the catalyst and at least one of a filler material and a binder material to provide a desired property or properties, e.g., desired catalyst dilution, mechanical strength and the like, to the solid particles. Such filler and binder materials, i.e., matrix material, are to some extent porous in nature and may or may not be effective to promote the desired chemical conversion. Such matrix materials include, for example, synthetic and naturally occurring substances, metal oxides, clays, silicas, aluminas, silica-aluminas, silica-magnesias, silica-zirconias, silica-thorias, silica-berylias, silica-titanias, silica-alumina-thorias, silica-alumina-zirconias, mixtures of these and the like.

If one or more matrix materials are included in the solid particles, the catalyst preferably comprises about 1% to about 99%, more preferably about 5% to about 90% and still more preferably about 10% to about 80%, by weight of the total solid particles.

The preparation of solid particles comprising CMSC and matrix materials is conventional and well known in the art and, therefore, need not be discussed in detail here. Certain of such preparation procedures are described in the patents and patent applications previously incorporated by reference herein, as well as in U.S. Pat. Nos. 3,140,253 and Re. 27,639. Catalysts which are formed during and/or as part of the methods of manufacturing the solid particles are within the scope of the present invention.

The solid particles including the catalysts may be of any size functionally suitable in the present invention. In order that the catalyst be utilized more effectively, the solid particles are preferably small relative to fixed bed solid particles used to promote similar chemical conversions. More preferably, the solid particles have a maximum transverse dimension, e.g., diameter, in the range of about 1 micron to about 500 microns, still more preferably about 25 microns to about 200 microns.

The catalyst and/or solid particles may be subjected to mechanical size reduction, e.g., grinding, crushing, milling and the like, in order to obtain the desired particle size. However, it is preferred that the solid particles including the catalyst be more smooth, and more preferably also more spherical, relative to solid particles of similar composition obtained by mechanical size reduction. Such particle smoothness and sphericity tends to improve the useful life of the catalyst. One particularly useful processing step to achieve such smoothness and sphericity is to employ spray drying as part of the solid particle manufacturing process to form the solid particles or precursors of the solid particles. An additional advantage of employing such spray drying is that the conditions of such a step can be controlled so that the product solid particles are of a desired particle size or size range. The use of spray drying in such catalyst-/solid particle manufacturing is conventional and well known, and therefore need not be discussed in detail here.

The non-zeolitic molecular sieves or NZMSs are particularly useful in the practice of the present invention. Among the NZMSs, the SAPOs are particularly useful. SAPO-17 and SAPO-34, which is described in detail in Example 38 of U.S. Pat. No. 4,440,871, are especially preferred catalysts for promoting the reaction of molecules containing one carbon atom, e.g., methane, methanol, methyl halide, and the like, to form products containing up to about 6, preferably up to about 4, carbon atoms per molecule, e.g., ethylene, propylene, butylene and the like. Currently, SAPO-34 is most preferred.

The amount of catalyst o solid particles in the reaction zone, may vary over a wide range depending, for example, on the specific processing application involved.

The present process is conducted such that the catalyst is present in the fluidized state, in one embodiment as a fluidized bed of solid particles.

The chemical conversion or reaction obtained by practicing the present invention can vary widely and depends, for example, on the feedstock and catalyst employed and on the feedstock/catalyst contacting conditions used. Substantially any chemical conversion or reaction which is capable of being catalyzed by a CMSC may be conducted while practicing the present invention. Examples of reactions which may be obtained include cracking; disproportionation; olefin production from non-olefin feedstocks; olefin interconversion; aldol, e.g., aldehyde-aldehyde, ketone-ketone, aldehyde-ketone and aldehyde or ketone-aromatic component, condensation; condensation reactions to produce cyclic lactams, isoprene formation; alkylation (aromatic, e.g., benzene, toluene and phenol alkylation); and isomerization (xylene isomerization). One particularly preferred chemical conversion or reaction involves olefin production from non-olefin feedstocks, more preferably feedstocks comprising aliphatic hetero compounds.

Substantially any feedstock or combination of feedstocks may be employed in the present invention. Such feedstock, i.e., reactant component or components, may be gaseous, solid or liquid at ambient conditions, i.e., 20° C. and atmospheric pressure. The feedstock may be inorganic, organic or a combination of inorganic and organic components. The present reaction system is particularly applicable to organic feedstocks, preferably having molecules comprising carbon and hydrogen, and more preferably at least one other element. This other element is preferably selected from the group consisting of oxygen, sulfur, halogen, nitrogen, phosphorus and mixtures thereof, with oxygen being particularly preferred.

As alluded to previously, the present invention is particularly useful in converting feedstocks having relatively small molecules, i.e., molecules having relatively small kinetic diameters. Thus, the feedstock preferably contains 1 to about 10, more preferably 1 to about 4, carbon atoms per molecule. Aliphatic hetero compounds are particularly preferred feedstocks for use in the present invention, especially when light olefins, i.e., olefins containing 2 to about 6 and preferably 2 to 4 carbon atoms per molecule, are to be produced. When light olefins are the desired product, such olefins are preferably produced as the major hydrocarbon product, i.e. over 50 mole percent of the hydrocarbon product is light olefins. The term "aliphatic hetero compounds" is employed herein to include alcohols, halides, mercaptans, sulfides, amines, ethers and carbonyl compounds (aldehydes, ketones, carboxylic acids and the like). The aliphatic moiety preferably contains from 1 to about 10 carbon atoms and more preferably contains from 1 to about 4 carbon atoms. Suitable reactants include lower straight or branched chain alkanols, their unsaturated counterparts, and the nitrogen, halogen and sulfur analogue of such. Representative of suitable aliphatic hetero compounds include: methanol; methyl mercaptan methyl sulfide; methyl amine; dimethyl ether; ethanol; ethyl mercaptan; ethyl chloride; diethyl ether; methyethyl ether; formaldehyde; dimethyl ketone; acetic acid; n-alkyl amines; n-alkyl halides and n-alkyl sulfides having n-alkyl group having 3 to 10 carbon atoms; and mixtures thereof. In one embodiment, e.g., where light olefins are the desired products, the feedstock is preferably selected from the group consisting of methanol, ethanol, dimethyl ether, diethyl ether and mixtures thereof, with methanol being particularly preferred.

In certain instances, it is preferred that the feedstock/catalyst contacting conditions be such that the contacting temperature exceed the critical temperature of the feedstock. In other words, in certain embodiments, the feedstock is preferably in the supercritical state at the step (a) feedstock/catalyst contacting conditions. Having the feedstock in the supercritical state is particularly useful when the feedstock contains 1 to about 10, more preferably 1 to about 4, carbon atoms per molecule.

The product or products obtained from the step (a) feedstock/catalyst contacting will, of course, depend, for example, on the feedstock, catalyst and conditions employed. As with the feedstock, the product or products can be inorganic, organic or a combination of inorganic and organic components. Preferably, the desired product is organic. However, it should be noted that a necessary, and therefore desired, reaction by-product may be inorganic even when the primary product sought is organic. This is exemplified by the conversion of methanol to light olefins plus water. The organic product or products have molecules which preferably include carbon and hydrogen. In one embodiment, the desired product preferably contains 1 to about 10, more preferably 1 to about 4, carbon atoms per molecule. The desired product or products preferably have kinetic diameters which allow such product or products to be removed from or escape from the pores of the CMSC.

In addition to the feedstock, a diluent may be used in conjunction with the feedstock if desired and/or beneficial to the overall process. Such diluent may be mixed or combined with the feedstock prior to the step (a) feedstock/catalyst contacting or it may be introduced into the reaction zone separately from the feedstock. Preferably, the feedstock and diluent are both substantially continuously fed to the reaction zone during step (a). Such diluent preferably acts to moderate the rate, and possibly also the extent, of feedstock chemical conversion and may also act to aid in temperature control. In certain embodiments, the diluent is preferably substantially continuously fed to the reaction zone during at least one of steps (b), (c), and (d), if step (d) is employed, more preferably during all these steps. This use of the diluent during the present process other than during step (a) tends to benefit the catalyst and improve process control. The presence of such diluent on a substantially continuous basis may allow for a smoother transition from one step of the process to the next step.

Typical of the diluents which may be employed in the instant process are helium, argon, nitrogen, carbon monoxide, carbon dioxide, hydrogen, water, hydrocarbons and mixtures thereof. When the feedstock contains 1 to about 6 carbon atoms per molecule, the diluent, if any, is preferably selected from the group consisting of helium, argon, nitrogen, carbon monoxide, carbon dioxide, hydrogen, water and mixtures thereof, with water, nitrogen and mixtures thereof, in particular water, being more preferred. The amount of diluent employed, if any, may vary over a wide range depending on the particular application involved. For example, the amount of diluent may be in an amount in the range of about 0.1% or less to about 99% or more of the moles of feedstock.

Step (a) of the present process often results in the catalyst losing at least a portion of at least one desirable property, e.g., catalytic property. The catalyst is contacted with regeneration medium in step (c) preferably to substantially maintain or improve the effectiveness of the catalyst to promote the desired chemical conversion. For example, the catalyst may become less effective due to formation of carbonaceous deposits or precursors of such deposits in the pores or other parts of the catalyst and/or solid particles during step (a). In one embodiment, the regeneration medium in step (c) acts to reduce the average kinetic diameter of molecules present in the pores of the catalyst. Such reduction in the kinetic diameter of these molecules is preferably sufficient to allow the resulting molecules to leave or exit the catalyst pores, thereby providing more pores and/or pore volume for the desired chemical conversion. In step (c), the catalyst in the reaction zone is regenerated, such as for example, by removing carbonaceous deposit material by oxidation in an oxygen-containing atmosphere.

In one embodiment, the catalyst includes at least one added component effective to promote the action of the regeneration medium. For example, the catalyst may include at least one metal component effective to promote the oxidation of the carbonaceous deposit material. Of course, such metal component should have no substantial adverse effect on the desired chemical conversion. The specific added catalyst component depends on the requirement of the particular application involved. Examples of such added components include components of transition metals, such as nickel, cobalt, iron, manganese, copper and the like; the platinum group metals such as platinum, palladium, rhodium and the like; and the rare earth metals such as cerium, lanthanum and the like, and mixtures thereof. If an added metal component is used, it is preferred that this component be present as a minor amount, more preferably as about 1 ppm to about 20%, by weight (calculated as elemental metal) of the weight of catalyst, including the matrix materials, employed.

Alternately to the oxidative catalyst regeneration, a reducing medium can be employed in step (c) to regenerate the catalyst. Such reducing medium, preferably selected from the group consisting of hydrogen, carbon monoxide and mixtures thereof, and in particular hydrogen, can, for example, be used to react with molecules, e.g., of carbonaceous deposit material precursor, in the pores of the catalyst to produce molecules of reduced kinetic diameter so that such produced molecules can exit the pores of the catalyst. In one embodiment, the reducing medium is hydrogen and the catalyst includes at least one component, preferably a metal component, effective to promote hydrogenation and/or hydrocracking of molecules present on the catalyst, e.g., in the pores of the catalyst, at the conditions of the reductive regeneration of step (c).

Combinations of oxidative and reductive catalyst regeneration may be employed. For example, the use of a reducing medium in step (a), e.g., as a diluent as discussed herein, may at least partially regenerate the catalyst, thereby prolonging the useful cycle life before the catalyst is subjected to a more complete oxidative regeneration. Of course, oxidative regeneration and reductive regeneration of the catalyst may be used, alone, as appropriate, rather than in combination.

In between steps (a) and (c), the catalyst is subjected to purging to minimize, preferably substantially eliminate, contact between the feedstock/product of step (a) and the regeneration medium/regeneration medium product of step (c). Such purging step or steps are often required to avoid a violent, even explosive reaction between these materials. The first purge medium of step (b) and the second purge medium of step (d) are chosen to effectively purge the catalyst, as described herein. Such purge media should have no substantial adverse effect on the catalyst or on the desired chemical conversion or reaction. The first purge medium is preferably substantially chemically inert relative to the feedstock and product (and diluent, if any) at the conditions at which step (a) occurs. The second purge medium is preferably substantially chemically inert relative to the regeneration medium and regeneration medium product at the conditions at which step (c) occurs.

The first and second purge media are preferably substantially gaseous at the conditions at which steps (a) and (c) occur, respectively. The amount and flowrate of these media employed may vary over a wide range, provided that such amount and flowrate are sufficient to effect steps (b) and (d), as desired. Excessive amounts and flowrates of such media should be avoided to control purge time and cost. Of course, sufficient purge media should be employed to effectively eliminate any dangerous conditions in the reaction zone. The purge media are preferably introduced into the reaction zone, at sufficiently high rates to aid in moving the solid particles in the reaction zone. This movement of the solid particles facilitates effective and efficient purging of the reaction zone.

The composition of the first and second purge media useful in the present invention may vary depending on the specific application involved. If suitable in the application involved, the first and second media may be independently selected from those materials from which the diluent, described herein, is selected. Preferably, at least one, more preferably both, of the first and second purge media and the diluent are the same material. In certain embodiments, the first and second purge media are preferably independently selected from the group consisting of water, nitrogen and mixtures thereof, in particular water.

The instant process may be carried out in a single reaction zone or a plurality of such zones arranged in series or in parallel. After the desired product or products are separated from the solid particles using, for example, solid/gas separation devices such as cyclone separators, various techniques, such as distillation, adsorption and the like, can be used to recover or purify such product or products. The same solid/gas separation devices are preferably used to separate the solid particles from the first and second purge media, the regeneration medium and the regeneration medium product or products. This multiple use of such separation devices is a substantial cost saving feature of the present invention. Because of the cyclic nature of the present process, in one embodiment it is preferred that a plurality of reaction zones be employed. It is preferred that the timing of steps (a), (b), (c) and (d) be predetermined so that a relatively constant amount of product passes from the reaction zones to the product separation subsystems. Thus, these product separation subsystems can be operated effectively on a substantially steady state basis.

The conditions at which step (a) occurs can vary widely depending, for example, on the specific feedstock and catalyst employed and on the specific product or products desired. The present process is particularly applicable with step (a) feedstock/catalyst contacting temperatures in excess of about 200° C., more preferably in excess of about 300° C., and with step (a) pressures in excess of about 10 psig., more preferably in excess of about 50 psig. If light olefins are to be produced from feedstock containing 1 to about 4 carbon atoms per molecule, step (a) temperatures are preferably in the range of about 200° C. to about 600° C. or even about 700° C., more preferably about 350° C. to about 550° C. and still more preferably about 400° to about 500° C., with step (a) pressures preferably below about 1500 psig. The pressure at which steps (b), (c) and (d) occur are preferably within about 100 psig, more preferably within about 50 psi of the step (a) pressure. In certain embodiments, the pressure in the reaction zone is maintained substantially constant through steps (a), (b), (c) and (d). The residence time of the feedstock in the reaction zone may be independently selected depending, for example on the specific feedstock and catalyst employed, and on the specific product or products desired.

The following non-limiting examples are provided to better illustrate the invention.

EXAMPLE 1

A material including a methanol to olefins catalyst used in certain of the following examples was prepared as follows.

A first slurry of 50% by weight SAPO-34 crystals and 50% by weight water was prepared and subjected to continuous mixing. In a separate vessel, a second, aqueous slurry of kaolin clay and aluminum hydroxychloride (which includes the equivalent of 23.4% by weight alumina, calculated as Al$_2$O$_3$) was prepared. The first slurry was added to the second slurry to form a combined slurry which was mixed for about 10 minutes. The combined slurry was then stone milled to obtain a substantially uniform particle distribution.

The milled slurry was then spray dried to produce particles having an average particle size of about 70 microns. The spray dried particles were calcined for two hours at 600° C.

The compositions of the first and second slurries were chosen so that the final particles contained 60% by weight SAPO-34, 23% by weight kaolin clay and 17% by weight Al$_2$O$_3$.

EXAMPLE 2 TO 26

An experimental apparatus used in Examples 2 to 26 was as follows:

The reactor was a 1 inch O.D. stainless steel fluidized bed with an extended disengagement zone at the top. The reactor had previously been coated internally with sodium silicate to minimize the catalytic activity of the reactor itself. The reactor was loaded with 97 grams of the material prepared in Example 1. The reactor temperature was controlled by the Techne SBL2-D fluidized sand bath in which the reactor was located. Analytical grade methanol was fed using a 150 rpm FMI metering pump with a model RHOCKC microhead. The methanol was vaporized and preheated in the feed lines to the reactor using heat tape. Methanol flow was measured by periodically timing the level change in a burette on the pump suction line. A small rotameter was also used to check the methanol flow.

Nitrogen diluent was fed from high pressure cylinders. It was mixed with the methanol upstream of the reactor. Nitrogen flow was controlled with a Veriflow controller, and measured with a rotameter.

Pressure in the reactor was controlled using a Grove pressure regulator on the reactor outlet. Pressure was reduced after the reactor outlet to about 5 psig. to avoid condensation in the sample lines. From the reactor, steam jacketed lines led to the gas chromatograph, then to the turbine flow meter used for measuring gas flows. Fittings and other potentially cool areas were electrically heated and insulated to prevent any condensation of water or heavy products in the sample lines. The gas stream then went to a condenser, through a wet test meter and was vented back to a hood.

Regeneration was controlled by a set of low wattage ASCO solenoid switching valves, which were controlled by an IBM PC driven ISAAC data acquisition and control system. At the beginning of a regeneration cycle the methanol feed was switched away from the reactor and through a recycle line back to the feed tank. Simultaneously, a nitrogen purge was switched onto the reactor and regeneration was started.

The reaction product was analyzed with a Varian 3700 gas chromatograph, containing two columns (Carbosieve S2 and Poropack R) with thermal conductivity and flame ionization detectors respectively. The system gave full stream analysis of all major components.

A series of experiments were run varying reaction temperature and pressure, and methanol and nitrogen flowrates.

Varying the above also varied the partial pressures of the reactants and products. The catalyst activity was 'fixed'. This was achieved by fully regenerating the catalyst prior to the start of each reaction run and selecting the sample time to give a product of weight hourly space velocity (WHSV) and sample time which, based on previous experience, had given good results.

Regeneration was started immediately after the gas chromatograph sample was taken. The fluidized sand bath temperature was raised to about 500° C. and air was fed to the reactor. Regeneration lasted for 2 hours. The nitrogen diluent continued to flow to the reactor throughout the regeneration. Nitrogen was fed by itself to the reactor for 2 minutes before the air was started and again before the reactor was returned to the reaction mode. This was to avoid unwanted reactions between oxygen and the methanol.

The results from the experiments were given in Table 1.

TABLE 1

| Run* Number | Sample Time, Min. | Temp °C. | Pressure psia | whsv | Dilution mole % | Dimethyl ether in Product, wt. % | MeOH Conv. % |
|---|---|---|---|---|---|---|---|
| 2 | 7.5 | 386 | 44.5 | 4.51 | 55.40 | 0.00 | 97.9 |

TABLE 1-continued

| Run* Number | Sample Time, Min. | Temp °C. | Pressure psia | whsv | Dilution mole % | Dimethyl ether in Product, wt. % | MeOH Conv. % |
|---|---|---|---|---|---|---|---|
| 3 | 6.0 | 411 | 86.7 | 2.95 | 68.49 | 3.22 | 89.2 |
| 4 | 6.0 | 379 | 65.2 | 2.05 | 74.43 | 0.00 | 94.9 |
| 5 | 20.0 | 413 | 96.5 | 4.10 | 62.23 | 2.16 | 91.7 |
| 6 | 22.0 | 390 | 51.5 | 3.74 | 63.76 | 2.12 | 89.6 |
| 7 | 36.0 | 395 | 55.2 | 2.12 | 69.81 | 1.16 | 95.6 |
| 8 | 20.0 | 391 | 84.1 | 3.96 | 64.95 | 2.33 | 88.2 |
| 9 | 19.0 | 415 | 89.2 | 4.34 | 63.44 | 2.16 | 91.5 |
| 10 | 36.0 | 401 | 72.1 | 2.65 | 74.95 | 3.25 | 88.2 |
| 11 | 36.0 | 433 | 89.5 | 2.68 | 68.56 | 3.40 | 90.0 |
| 12 | 24.0 | 402 | 86.7 | 3.46 | 62.82 | 61.44 | 3.1 |
| 13 | 37.0 | 433 | 57.2 | 2.29 | 72.45 | 1.57 | 96.1 |
| 14 | 36.0 | 431 | 51.8 | 2.38 | 72.72 | 1.17 | 97.1 |
| 15 | 36.0 | 419 | 83.9 | 2.44 | 64.62 | 1.26 | 96.8 |
| 16 | 24.0 | 422 | 86.5 | 3.49 | 64.51 | 2.82 | 90.2 |
| 17 | 19.0 | 423 | 62.9 | 2.20 | 76.21 | 0.86 | 97.0 |
| 18 | 24.0 | 400 | 58.4 | 4.03 | 62.33 | 2.71 | 86.9 |
| 19 | 20.0 | 399 | 78.6 | 4.79 | 50.86 | 4.99 | 77.0 |
| 20 | 36.0 | 413 | 87.3 | 2.56 | 75.07 | 3.23 | 87.9 |
| 21 | 20.0 | 425 | 90.0 | 4.07 | 64.96 | 3.41 | 87.1 |
| 22 | 36.0 | 433 | 91.9 | 2.74 | 60.86 | 4.89 | 85.8 |
| 23 | 19.0 | 396 | 70.9 | 4.30 | 62.06 | 4.10 | 79.8 |
| 24 | 36.0 | 425 | 84.4 | 1.84 | 77.78 | 1.49 | 96.5 |
| 25 | 17.0 | 386 | 89.4 | 4.81 | 51.18 | 29.80 | 34.5 |
| 26 | 19.0 | 376 | 58.2 | 4.15 | 58.26 | 21.34 | 42.0 |

*There was over 2% by weight of carbon formed on the catalyst particles in each run.

| | SELECTIVITY TO VARIOUS PRODUCTS, WT. % OF HYDROCARBON PRODUCT | | | | | | | |
|---|---|---|---|---|---|---|---|---|
| Run Number | $CH_4$ | $C_2H_4$ | $C_2H_6$ | $C_3H_6$ | $C_3H_8$ | $C_4H_8$'s | $C_{5+}$ | Total Olefins |
| 2 | 0.58 | 20.52 | 0.83 | 43.73 | 10.64 | 20.97 | 2.74 | 85.22 |
| 3 | 0.81 | 30.90 | 1.77 | 51.70 | 5.41 | 8.59 | 0.82 | 91.19 |
| 4 | 0.55 | 23.66 | 1.03 | 53.05 | 6.15 | 14.12 | 1.45 | 90.83 |
| 5 | 0.73 | 27.15 | 1.75 | 51.78 | 6.84 | 10.81 | 0.94 | 89.74 |
| 6 | 0.60 | 26.39 | 1.03 | 51.14 | 5.85 | 13.51 | 1.47 | 91.04 |
| 7 | 0.59 | 24.69 | 1.23 | 51.44 | 6.69 | 14.05 | 1.31 | 90.18 |
| 8 | 0.68 | 24.52 | 1.36 | 51.52 | 7.40 | 12.85 | 1.68 | 88.89 |
| 9 | 0.73 | 26.75 | 1.75 | 50.72 | 7.02 | 11.20 | 1.83 | 88.67 |
| 10 | 0.67 | 31.23 | 1.29 | 53.02 | 5.02 | 7.82 | 0.95 | 92.07 |
| 11 | 1.02 | 32.48 | 2.08 | 50.84 | 5.18 | 7.61 | 0.79 | 90.93 |
| 12 | 14.04 | 30.11 | 2.88 | 22.38 | 5.25 | 20.37 | 4.98 | 72.86 |
| 13 | 0.91 | 32.47 | 1.89 | 48.23 | 6.71 | 8.74 | 1.06 | 89.44 |
| 14 | 0.89 | 31.24 | 1.78 | 47.27 | 7.25 | 10.23 | 1.34 | 88.74 |
| 15 | 0.83 | 25.48 | 2.13 | 49.54 | 8.62 | 12.26 | 1.12 | 87.28 |
| 16 | 0.77 | 29.34 | 1.85 | 50.94 | 6.17 | 10.08 | 0.85 | 90.36 |
| 17 | 0.87 | 24.46 | 1.79 | 40.41 | 11.49 | 18.24 | 2.74 | 83.11 |
| 18 | 0.60 | 28.96 | 1.07 | 51.18 | 4.96 | 11.94 | 1.29 | 92.08 |
| 19 | 0.77 | 28.58 | 1.41 | 48.58 | 7.13 | 11.98 | 1.56 | 89.14 |
| 20 | 0.73 | 31.66 | 1.60 | 53.10 | 4.74 | 7.15 | 1.01 | 91.91 |
| 21 | 0.78 | 29.93 | 1.76 | 50.18 | 5.92 | 10.15 | 1.28 | 90.26 |
| 22 | 1.10 | 33.96 | 2.16 | 49.90 | 4.86 | 7.17 | 0.85 | 91.03 |
| 23 | 0.67 | 28.03 | 1.13 | 50.23 | 5.75 | 12.62 | 1.57 | 90.88 |
| 24 | 0.92 | 27.46 | 2.03 | 46.89 | 8.51 | 13.12 | 1.07 | 87.47 |
| 25 | 1.72 | 27.30 | 3.27 | 38.57 | 13.00 | 13.11 | 3.03 | 78.98 |
| 26 | 1.28 | 27.24 | 1.86 | 40.66 | 11.71 | 14.67 | 2.58 | 82.57 |

These experiments demonstrate the feasibility of conducting chemical conversion, e.g., methanol to light olefins, in a moving, e.g., fluidized bed, catalyst system in a single reaction vessel. Much wear and tear on the catalyst is avoided since the catalyst need not be transported between a reaction vessel and a separate regeneration vessel. Since only one vessel is required, substantial capital cost savings can be achieved.

EXAMPLE 27

The experimental apparatus used in Example 27 was the same as used in Examples 2 to 26 except that the reactor was a one-inch quartz tube with internal filters and an extended three-inch disentrainment zone at the top. The reactor was loaded with a quantity of the material prepared in Example 1.

The reactor was repeatedly operated through the following cycle:

| | |
|---|---|
| Methanol Reaction Time | 15 Minutes |
| Purge Time | 4 Minutes |
| Catalyst Regeneration Time | 7 Minutes |
| Purge Time | 4 Minutes |

Total pressure in the reactor was maintained at 22.0 to 22.4 psia. Temperature was maintained at 480° C. throughout the cycle. During methanol reaction, the methanol WHSV was 1.83 to 1.87 hr.$^{-1}$. A substantially constant flow of nitrogen was provided throughout the cycle so that during methanol reaction the nitrogen was 78.3 to 78.6 mole % of the total feed to the reactor. Oxygen was used as the regeneration medium and the partial pressure of oxygen during catalyst regeneration was 1.54 to 1.56 psia.

A sample of reaction product was taken at six (6) minutes into the methanol reaction segment of each cycle and analyzed. Selected results from these analyses are given in Table 2.

| SELECTIVITY TO VARIOUS PRODUCTS,[1][2] WT. % OF HYDROCARBON PRODUCT | | | | | | | |
|---|---|---|---|---|---|---|---|
| No. of Catalyst Regenerations | $CH_4$ | $C_2H_4$ | $C_2H_6$ | $C_3H_6$ | $C_3H_8$ | $C_4H_8$ | $C_{5+}$ |
| 1 | 1.22 | 45.39 | 0.82 | 35.13 | 2.56 | 11.74 | 2.97 |
| 2 | 1.37 | 45.21 | 0.78 | 35.34 | 2.47 | 12.05 | 2.61 |
| 5 | 1.65 | 45.07 | 0.72 | 35.49 | 2.31 | 11.78 | 2.43 |
| 6 | 1.71 | 45.25 | 0.70 | 35.68 | 2.25 | 11.64 | 2.31 |
| 7 | 1.82 | 45.67 | 0.70 | 35.79 | 2.18 | 11.24 | 2.11 |

[1]Methanol conversion ranged from 99.4 to 99.8%.
[2]Dimethyl ether in the product ranged from 0.2 to 0.6 wt. %.

These results demonstrate that conducting chemical conversion, e.g., methanol to light olefins, in a single reaction vessel using fluidized catalyst can provide substantially steady state operation. This type of operation allows effective and efficient downstream processing, e.g., separation, of the reaction products.

EXAMPLE 28

A commercially sized fluidized bed reaction system is constructed to produce 5000 barrels per day of mixed ethylene and propylene from methanol. The system includes three reactor vessels in parallel. Each of the reactor vessels are equipped with a number of cyclone separators to aid in removing gases from the reactor vessel while holding the catalyst inside. The system also includes a conventional product handling/separation subsystem to recover and purify the products to the extent desired.

The feed system to each of the reactor vessels includes a separate steam inlet. Steam is substantially continuously fed to each of the vessels. A valved methanol inlet and a valved air inlet are also provided to each of the vessels. The methanol and air inlets are controlled so that only one of methanol or air is fed to any one reactor vessel at any one time.

Each of these reactor vessels are operated on the following reaction/regeneration cycle. Catalyst, similar in composition to that prepared in Example 1, is placed in the reaction vessel and heated to a temperature of 500° C. Vaporized and heated methanol is fed to the vessel (along with the steam diluent) to produce light olefins which are removed from the vessel through the cyclone separators. At this point the cycle is begun again. Throughout the cycle the catalyst is maintained at a temperature of about 500° C. and a pressure of about 80 psig. After a period of time, methanol flow is stopped and steam purges the vessel of methanol. After the purge, air is introduced into the reactor vessel to regenerate the catalyst. After the desired catalyst regeneration, the flow of air is stopped and steam purges the vessel of air. At this point, the cycle is begun again. The time sequencing of this cyclic operation is such that no less than two of the reactor vessels operate in the reaction mode at any one time.

This cyclic operation is effective in producing ethylene and propylene, in particular ethylene, from methanol.

While the present invention has been described with respect to various specific examples and embodiments, it is to be understood that the invention is not limited thereto and that it can be variously practiced within the scope of the following claims.

What is claimed is:

1. A cyclic process for catalytically converting a feedstock containing one or more compounds selected from the group consisting of alcohols, halides, mercaptans, sulfides, amines, ethers and carbonyl compounds, said compounds having from 1 to about 4 carbon atoms per molecule, into a product containing light olefins in a fluidized bed reaction zone which comprises the sequential steps of:
   (a) contacting said feedstock with a fluidized mass of solid particles comprising crystalline microporous three-dimensional solid catalyst in said reaction zone at conditions effective to convert said feedstock into said product and to form carbonaceous deposit material on said catalyst;
   (b) discontinuing said feedstock contacting and then contacting said particles with a first purge medium within said reaction zone to reduce the amount of at least one of said feedstock and said product in contact with said particles; and
   (c) discontinuing said first purge contacting and then contacting said particles with regeneration medium within said reaction zone at conditions effective to remove at least a portion of said carbonaceous deposit material from said catalyst, provided that steps (a), (b) and (c) are repeated periodically.

2. The process of claim 1 wherein the conditions at which steps (a), (b) and (c) are conducted and the frequency of periodically repeating steps (a), (b) and (c) are selected to control the temperature within said reaction zone during steps (a), (b) and (c) within a temperature range of about 100° C.

3. The process of claim 1 which further comprises withdrawing a portion of said catalyst from said reaction zone; contacting said withdrawn catalyst with a regeneration medium at conditions that are more severe than said conditions in step (c), said treating conditions being effective to further remove said carbonaceous deposit material from said withdrawn catalyst, to produce a treated catalyst; and returning said treated catalyst to said reaction zone.

4. The process of claim 1 wherein said regeneration medium comprises oxygen.

5. The process of claim 1 wherein said particles have a particle diameter in the range of about 1 micron to about 500 microns.

6. The process of claim 1 wherein said catalyst is selected from the group consisting of layered clays, zeolitic molecular sieves, non-zeolitic molecular sieves and mixtures thereof.

7. The process of claim 1 wherein said catalyst is selected from the group consisting of non-zeolitic molecular sieves and mixtures thereof.

8. The process of claim 1 wherein said catalyst has pores with an effective diameter of less than about 5 Angstroms.

9. The process of claim 1 wherein said catalyst is selected from the group consisting of silicoaluminophosphates and mixtures thereof.

10. The process of claim 1 wherein said solid particles contain about 1 to about 99% by weight of said catalyst.

11. The process of claim 1 wherein a plurality of said reaction zones are arranged in parallel, each of said reaction zones undergoing steps (a), (b) and (c).

12. A cyclic process for catalytically converting a feedstock containing one or more compounds selected from the group consisting of alcohols, halides, mercaptans, sulfides, amines, ethers and carbonyl compounds, said compounds having from 1 to about 4 carbon atoms per molecule, into a product containing light olefins in a fluidized bed reaction zone which comprises the sequential steps of:
   (a) contacting said feedstock with a fluidized mass of said particles comprising crystalline microporous silicoaluminophosphate (SAPO) molecular sieve catalyst having pores with an effective diameter less than about 5 Å in said reaction zone at conditions effective to convert said feedstock into said product and to form a carbonaceous deposit material on said catalyst;
   (b) discontinuing said feedstock contacting and then contacting said particles with a first purge medium within said reaction zone to reduce the amount of at least one of said feedstock and said product in contact with said particles; and
   (c) discontinuing said first purge contacting and then contacting said particles with regeneration medium within said reaction zone at conditions effective to remove at least a portion of said carbonaceous deposit material from said catalyst, provided that steps (a), (b) and (c) are repeated periodically.

13. The process of claim 12 which further comprises (d) discontinuing said regeneration contacting and then contacting said particles with a second purge medium within said reaction zone to reduce the amount of at least one of said regeneration medium and regeneration medium product in contact with said particles, provided that steps (a), (b), (c) and (d) are repeated periodically.

14. The process of claim 12 wherein said regeneration medium comprises oxygen.

15. The process of claim 12 wherein said catalyst includes at least one added component effective to promote the removal of said carbonaceous deposit material during step (c).

16. The process of claim 15 wherein said added component is a metal component.

17. The process of claim 15 wherein said regeneration medium is hydrogen and said added component is effective to promote at least one of the hydrogenation and hydrocracking of molecules present on said catalyst at the conditions of step (c).

18. The process of claim 12 wherein said catalyst is selected from the group consisting of SAPO-34, SAPO-17 and mixtures thereof.

19. The process of claim 12 wherein said feedstock is selected from the group consisting of methanol, ethanol, dimethyl ether, diethyl ether and mixtures thereof.

20. The process of claim 12 wherein said step (a) occurs in the presence of at least one diluent.

21. The process of claim 20 wherein said feedstock and said diluent are both substantially continuously fed to said reaction zone during step (a).

22. The process of claim 21 wherein said diluent is substantially continuously fed to said reaction zone during at least one of steps (b) and (c).

23. The process of claim 20 wherein said diluent is selected from the group consisting of helium, argon, nitrogen, carbon monoxide, carbon dioxide, hydrogen, water and mixtures thereof.

24. The process of claim 20 wherein said diluent is selected from the group consisting of nitrogen, water and mixtures thereof.

25. The process of claim 20 wherein said diluent comprises water.

26. The process of claim 12 wherein said product contains ethylene, propylene, butylene and mixtures thereof.

27. The process of claim 12 wherein the conditions at which steps (a), (b) and (c) are conducted and the frequency of periodically repeating steps (a), (b) and (c) are selected to control the temperature within said reaction zone during steps (a), (b) and (c) within about 100° C. of the average temperature at which step (c) takes place.

28. The process of claim 12 which further comprises withdrawing a portion of said catalyst from said reaction zone; contacting said withdrawn catalyst with a regeneration medium at conditions that are more severe than said conditions in step (c), said treating conditions being effective to further remove said carbonaceous deposit material from said withdrawn catalyst, to produce a treated catalyst; and returning said treated catalyst to said reaction zone.

* * * * *